United States Patent
Hong et al.

(10) Patent No.: US 10,464,974 B2
(45) Date of Patent: Nov. 5, 2019

(54) _NEUROSPORA CRASSA_ STRAINS WITH AMPLIFIED EXPRESSION OF CELLULASES AND PRODUCTION OF BIOFUEL THEREFROM

(71) Applicant: University of Cincinnati, Cincinnati, OH (US)

(72) Inventors: Christian Hong, Cincinnati, OH (US); Toru Matsuura, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 15/542,104

(22) PCT Filed: Jan. 8, 2016

(86) PCT No.: PCT/US2016/012565
§ 371 (c)(1),
(2) Date: Jul. 7, 2017

(87) PCT Pub. No.: WO2016/112238
PCT Pub. Date: Jul. 14, 2016

(65) Prior Publication Data
US 2018/0273589 A1    Sep. 27, 2018

Related U.S. Application Data

(60) Provisional application No. 62/101,613, filed on Jan. 9, 2015.

(51) Int. Cl.
| | | |
|---|---|---|
| *C12P 7/10* | (2006.01) | |
| *C12P 19/02* | (2006.01) | |
| *C12P 19/14* | (2006.01) | |
| *C12N 9/42* | (2006.01) | |
| *C12N 15/80* | (2006.01) | |
| *C07K 14/37* | (2006.01) | |

(52) U.S. Cl.
CPC ............ *C07K 14/37* (2013.01); *C12N 9/2437* (2013.01); *C12N 15/80* (2013.01); *C12P 7/10* (2013.01); *C12P 19/02* (2013.01); *C12P 19/14* (2013.01); *C12P 2203/00* (2013.01); *C12Y 101/99018* (2013.01); *C12Y 302/01004* (2013.01); *C12Y 302/01021* (2013.01); *C12Y 302/01091* (2013.01); *Y02E 50/16* (2013.01)

(58) Field of Classification Search
CPC ...... C07K 14/37; C12N 9/2437; C12N 15/80; C12P 19/14; C12P 19/02; C12P 7/10; C12P 2203/00; C12Y 302/01021; C12Y 302/01004; C12Y 101/99018; C12Y 302/01091; Y02E 50/16

See application file for complete search history.

(56) References Cited

U.S. PATENT DOCUMENTS

| | | | |
|---|---|---|---|
| 2013/0081153 A1* | 3/2013 | Dolan | C12N 15/8261 800/278 |
| 2014/0045243 A1 | 2/2014 | Znameroski et al. | |
| 2014/0106408 A1 | 4/2014 | Mitchinson et al. | |
| 2014/0220641 A1 | 8/2014 | Tian et al. | |

FOREIGN PATENT DOCUMENTS

| | | | | |
|---|---|---|---|---|
| WO | WO-2012125865 A1 * | 9/2012 | ..... | C12Y 302/01021 |
| WO | WO-2013022594 A1 * | 2/2013 | ..... | C07K 14/37 |

OTHER PUBLICATIONS

Sousa et al., Microbiology 148(Pt5):1291-1303, 2002.*
Mohr et al. (Nucleic Acids Research 28(7):1514-1524, 2000.*
Coradetti et al, "Conserved and essential transcription factors for cellulase gene expression in ascomycete fungi," Proceedings of the National Academy of Sciences of the United States of America, May 1, 2012, vol. 109, No. 19, pp. 7397-7402.
Schmoll et al, "Unravelling the molecular basis for light modulated cellulase gene expression—the role of photoreceptors in Neurospora crassa," BMC Genomics, Mar. 31, 2012, vol. 13, pp. 1-18.
International Search Report for corresponding Application No. PCT/US2016/012565 dated Mar. 18, 2016.
Matsuura, T. et al.: "Development of the Synthetic Gene Circuits to Amplify the Production of Biomaterials, Cellulases, and Lentivirus", Biophysical Journal, Feb. 16, 2016. 110(3), p. 317a.
Extended European Search Report pertaining to EP Application No. 16735441.4 dated Oct. 25, 2018.

* cited by examiner

*Primary Examiner* — Delia M Ramirez
(74) *Attorney, Agent, or Firm* — Dinsmore & Shohl LLP

(57) ABSTRACT

Transgenic strains of *Neurospora crassa* engineered to comprise a synthetic positive feedback loop for a transcriptional activator of cellulase expression such that cellulase production is amplified are disclosed, along with compositions thereof. The transgenic strains are particularly useful in methods for generating purified cellulases, fermentable sugars, and cellulosic ethanol for the efficient production of biofuel from cellulose-containing biomass and waste.

16 Claims, 9 Drawing Sheets

TABLE 1. THE FOLDER CHANGES OF THE CELLULOSE RELATING GENES BY AVICEL STIMULATION

| Name of strains | clr-1 | clr-2 | cbh-1 | gh6-2 | gh5-1 |
|---|---|---|---|---|---|
| 74A | $0.52 \times 10^1 \pm 0.32 \times 10^1$ | $1.26 \times 10^2 \pm 1.78 \times 10^2$ | $3.05 \times 10^2 \pm 2.83 \times 10^2$ | $1.94 \times 10^2 \pm 1.95 \times 10^2$ | $7.97 \times 10^1 \pm 7.38 \times 10^1$ |
| 328-4 | $0.53 \times 10^1 \pm 0.07 \times 10^1$ | $1.16 \times 10^2 \pm 1.47 \times 10^1$ | $1.03 \times 10^2 \pm 9.78 \times 10^0$ | $5.53 \times 10^1 \pm 1.15 \times 10^1$ | ND |
| 3KO-Δcre-1 | $0.33 \times 10^1 \pm 0.02 \times 10^1$ | $3.52 \times 10^1 \pm 3.25 \times 10^0$ | $1.70 \times 10^3 \pm 1.92 \times 10^2$ | $2.73 \times 10^3 \pm 3.91 \times 10^2$ | $1.85 \times 10^3 \pm 7.58 \times 10^1$ |
| Pcbh-1-clr-1 (74A) | $2.92 \times 10^1 \pm 0.18 \times 10^1$ | $3.57 \times 10^2 \pm 2.65 \times 10^1$ | $1.14 \times 10^3 \pm 2.18 \times 10^1$ | $6.49 \times 10^2 \pm 5.39 \times 10^1$ | $1.94 \times 10^3 \pm 2.37 \times 10^2$ |
| Pcbh-1-clr-2 (328-4) | $2.89 \times 10^1 \pm 0.50 \times 10^1$ | $4.89 \times 10^3 \pm 1.19 \times 10^3$ | $1.73 \times 10^4 \pm 1.36 \times 10^3$ | $1.38 \times 10^4 \pm 7.40 \times 10^1$ | $2.84 \times 10^2 \pm 2.79 \times 10^1$ |
| Pcbh-1-clr-2 (3KO-Δcre-1) #2 | $1.45 \times 10^1 \pm 0.14 \times 10^1$ | $4.22 \times 10^4 \pm 3.84 \times 10^3$ | $2.09 \times 10^4 \pm 9.10 \times 10^2$ | $1.36 \times 10^4 \pm 1.28 \times 10^3$ | $3.59 \times 10^4 \pm 4.97 \times 10^3$ |
| Pcbh-1-clr-2 (3KO-Δcre-1) #5 | $1.64 \times 10^1 \pm 0.05 \times 10^1$ | $1.55 \times 10^5 \pm 1.58 \times 10^4$ | $2.05 \times 10^4 \pm 3.46 \times 10^3$ | $1.25 \times 10^4 \pm 8.00 \times 10^2$ | $3.90 \times 10^4 \pm 4.33 \times 10^3$ |

THE FOLDER CHANGES IN THE TARGET GENES RELATIVE TO UNSTIMULATED 74A. AVERAGE ± SD (n=3)

FIG. 5

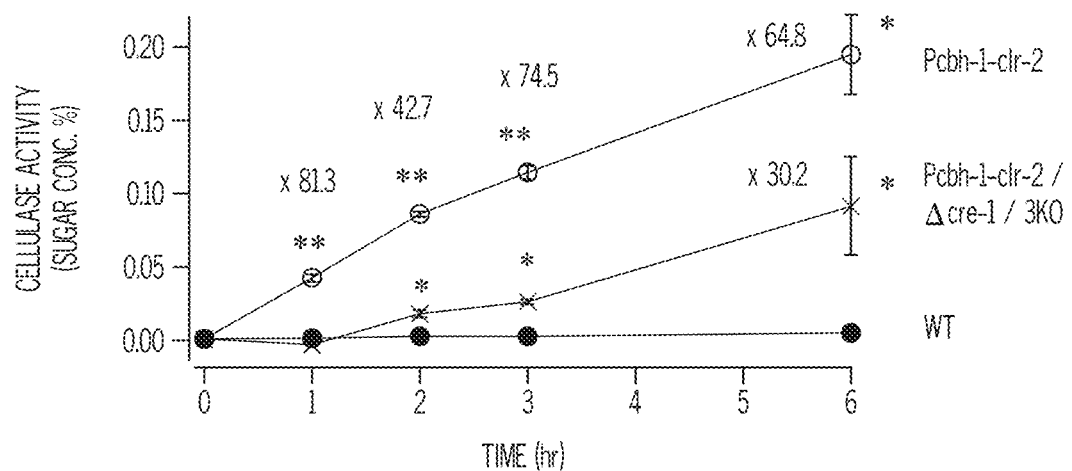
A
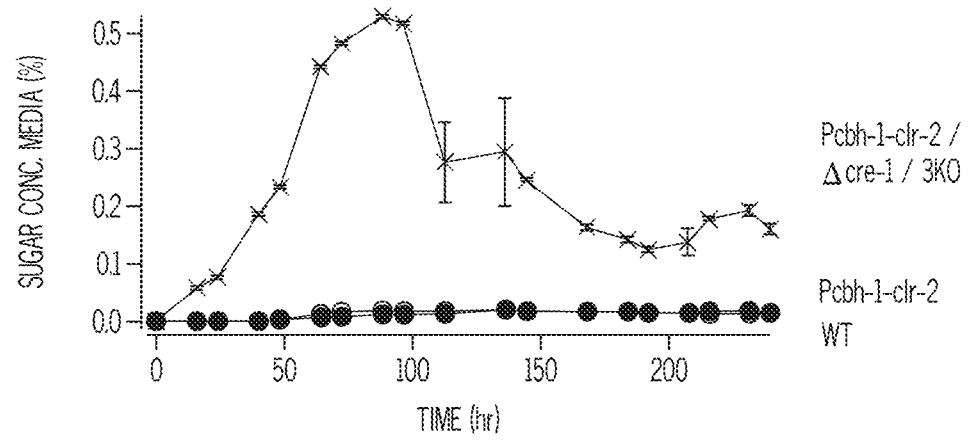
B
FIG. 6

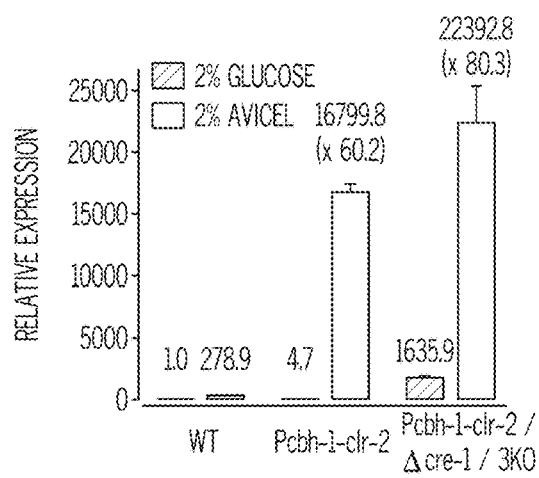
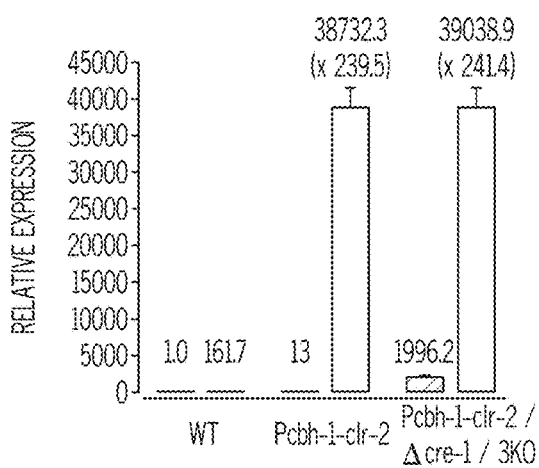
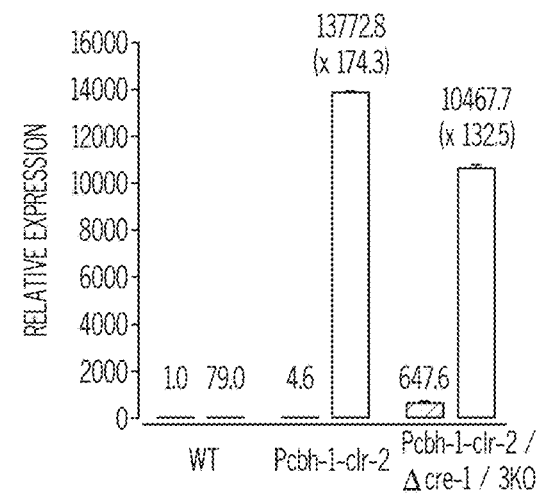
FIG. 9

NEUROSPORA CRASSA STRAINS WITH AMPLIFIED EXPRESSION OF CELLULASES AND PRODUCTION OF BIOFUEL THEREFROM

PRIORITY CLAIM

This application claims priority under 35 U.S.C. § 119(e) to U.S. Provisional application No. 62/101,613 filed with the USPTO on Jan. 9, 2015, the entire disclosure of which is incorporated herein in its entirety.

STATEMENT REGARDING FEDERALLY SPONSORED RESEARCH OR DEVELOPMENT

This invention was made with government support under D12AP00005 awarded by Defense Advanced Research Projects Agency (DARPA). The government has certain rights in the invention.

TECHNICAL FIELD

The disclosure relates to more efficient processes for generating cellulase enzymes involved in the production of biofuels from cellulose.

BACKGROUND

Second-generation biofuels, which are derived from biomass, have attracted worldwide attentions as a renewable energy source. Suitable feed stocks for the first-generation biofuels production are corn, wheat, sugarcane, soybean, grapes, seed and sunflowers. A major problem with these feed stocks is that they are also used for food and feed production and resource/land allocation is competitive with food production. To circumvent a conflict between demand for biofuel and food sources, cellulose-containing food waste and wood chips have been used as substrates for the second-generation biofuels. Breakdown of cellulose to sugar molecules is a required step before the fermentation process for ethanol production. However, a drawback in the development of this technology is that industrial-scale hydrolysis of cellulose is an expensive process due in large part to the cost of cellulases, the enzymes that degrade cellulose.

Cellulose is contained in nearly every natural, free-growing plant, tree, and bush, in meadows, forests, and fields all over the world without agricultural effort or cost needed to make it grow. One of the benefits of cellulosic ethanol is it reduces greenhouse gas emissions (GHG) by 85% over reformulated gasoline. By contrast, starch ethanol (e.g., from corn), which most frequently uses natural gas to provide energy for the process, may not reduce GHG emissions at all depending on how the starch-based feedstock is produced. According to the National Academy of Sciences as of 2011, there is no commercially feasible bio-refinery in existence capable of cost-effectively converting cellulosic biomass to fuel.

Ethanol is produced mostly from sugars or starches obtained from fruits and grains. In contrast, cellulosic ethanol is obtained from cellulose, the main component of wood, straw, and much of the structure of plants. Since cellulose cannot be digested by humans, the production of cellulose does not compete with the production of food. Moreover, since cellulose is the main component of plants, the whole plant can be harvested. This results in much better yields-up to 10 short tons per acre (22 t/ha), instead of 4-5 short tons/acre (9-11 t/ha) for the best crops of grain.

An estimated 323 million tons of cellulose-containing raw materials which could be used to create ethanol are thrown away each year in US alone. Furthermore, even land considered marginal for agricultural use could be planted with cellulose-producing crops, such as switchgrass, conceivably resulting in enough production to substitute for all the current oil imports into the United States.

Clearly there is a critical need in the art for more efficient methods for producing cellulases from cellulosic biomass for the cost-effective mass production of second-generation biofuels.

SUMMARY

Accordingly, transgenic strains of *Neurospora crassa*, a common type of red bread mold, have been developed to improve the current cellulase production system and to increase the efficiency of second-generation biofuel production with amplified expression of cellulases. *N. crassa* is found ubiquitously in nature in tropical and subtropical climates, and is commonly found growing on plant matter subsequent to fire. The *N.crassa* genome is about 43 megabases long and includes approximately 10,000 genes. Not only has it been fully sequenced since 2003, a project to produce knockout strains of ever *N. crassa* gene is well underway. Comprehensive information and access to strains and related materials is available to the public through the Fungal Genetics Stock Center (www.fgsc.net).

One embodiment provides transgenic strains of *Neurospora crassa* engineered to comprise a synthetic positive feedback loop for a transcriptional activator of cellulase expression. Other embodiments provide compositions comprising at least one of the inventive transgenic strains of *N. crassa* and an amount of culturing media.

Another embodiment is directed to a method for increasing expression of at least one cellulase in a cellulase-producing fungus, the method comprising engineering a strain of the cellulase-producing fungus comprising a synthetic positive feedback loop functional to increase expression of a transcriptional activator of cellulase expression.

Still other embodiments provide methods for producing a reducing sugar from cellulose-containing substrates. The methods comprise: culturing one or more transgenic strains of *Neurospora crassa* engineered for amplified production of cellulases in a culture media; optionally, harvesting the cellulases from the culturing media; and treating the cellulose-containing substrates with the culturing media or the harvested cellulases.

Methods for producing cellulosic ethanol from cellulose-containing substrates, which may then be processed into biofuels, are also provided. The methods comprising: culturing one or more transgenic strains of *Neurospora crassa* engineered for amplified production of cellulases in a culture media; optionally, harvesting the cellulases from the culturing media; treating the cellulose-containing substrates with the culturing media or the harvested cellulases to produce a fermentable sugar; fermenting the sugar by treatment with a yeast; and distilling the cellulosic ethanol.

All references (e.g., printed publications such as books, papers, patents, patent applications, catalogs, databases) are incorporated herein by reference. In the event of a conflict or inconsistency, the present specification, as modified by any amendments thereto, shall control.

These and other embodiments will be more clearly understood by reference to the detailed disclosure and accompanying figures.

BRIEF DESCRIPTION OF THE FIGURES

FIG. 5. Table 1, setting forth the fold changes in expression of five cellulose-related genes in six different strains subject to/caused by avicel stimulation.

FIG. 6. Graph of reducing sugar concentration (cellulase activity) versus time of incubation at 50° C. in 2% Avicel for three *Neurospora* strains: Pcbh-1-clr-2, Pcbh-1-clr-2/Δcre-1/3KO, and WT.

FIG. 9. (A) bar graph showing expression of cbh-1 in three strains, WT, Pcbh-1-clr-2, and Pcbh-1-clr-2-3KO-Δcre-1, as a function of whether glucose or Avicel is in the culturing media; (B) bar graph showing expression of gh5-1 in three strains as a function of culturing media; (C) bar graph showing expression of gh6-3 in same three strains as a function of culturing media.

DETAILED DESCRIPTION 140 billion gallons of gasoline (340 billion dollars) were consumed world-wide in 2014. 14 billion gallons of corn ethanol was produced in 2010 (Projection: 15 billion gallons in 2015). 0.33 million gallons of cellulosic biofuel was produced in 2014. The cost of corn ethanol is $1.92/gallon, and the enzyme is 3 cents/gallon. In contrast, the cost of cellulosic ethanol is $2.15/gallon, and the enzyme is 30 cents/gallon (NREL, 2012). Reduction of the cost of cellulases will lower the cost of cellulosic ethanol below corn ethanol and provide a cost-effective fuel alternative while lowering $CO_2$ emissions.

The model filamentous fungus, *Neurospora crassa* (*N. crassa*), is commonly found in tropical and sub-tropical regions on dead plant biomass, and is known for degrading cellulose as source of carbon. *N. crassa* is predicted to have twice as many cellulases compared to the known industrial strain *Trichoderma reesei*. The degradation of cellulose to sugars is achieved by the cooperative action of multiple cellulases. CLR-1, CLR-2, and XLR-1 are known as transcriptional activators, which regulate the expression of numerous cellulase genes in *N. crassa*. Multiple types of cellulases (40 cellulase genes in *Neurospora*) cooperatively work to degrade cellulose. Therefore, overexpression of multiple cellulose enzymes is necessary for efficient degradation. Current technology utilizes: (1) overexpression of each cellulase, one at a time (N. Louise Glass, UC Berkeley), and (2) genetic modification of the enzyme activity (National Renewable Energy Laboratory (NREL), Denver).

The present invention provides novel transgenic *N. crassa* strains and methods that permit a dramatic increase in expression of a large number of different cellulases suitable for industrial-scale applications. According to embodiments of the invention, a synthetic positive feedback loop is provided and engineered into the strain that maximizes the expression of key regulatory factors that trigger amplified-expression of multiple types of cellulases by the transgenic *N. crassa*. *N. crassa* strains comprising an embodiment of the positive feedback circuit may be utilized to produce large quantities of cellulases. Cellulases are secreted into the culturing media and may be isolated and purified for use in, e.g. food processing, as digestive enzymes for medical purposes, as a component of cleaning formulations, in processes for tenderization of fibers such as cotton, and, significantly, in production of sugars for cellulosic ethanol and biofuel.

Figure 1:
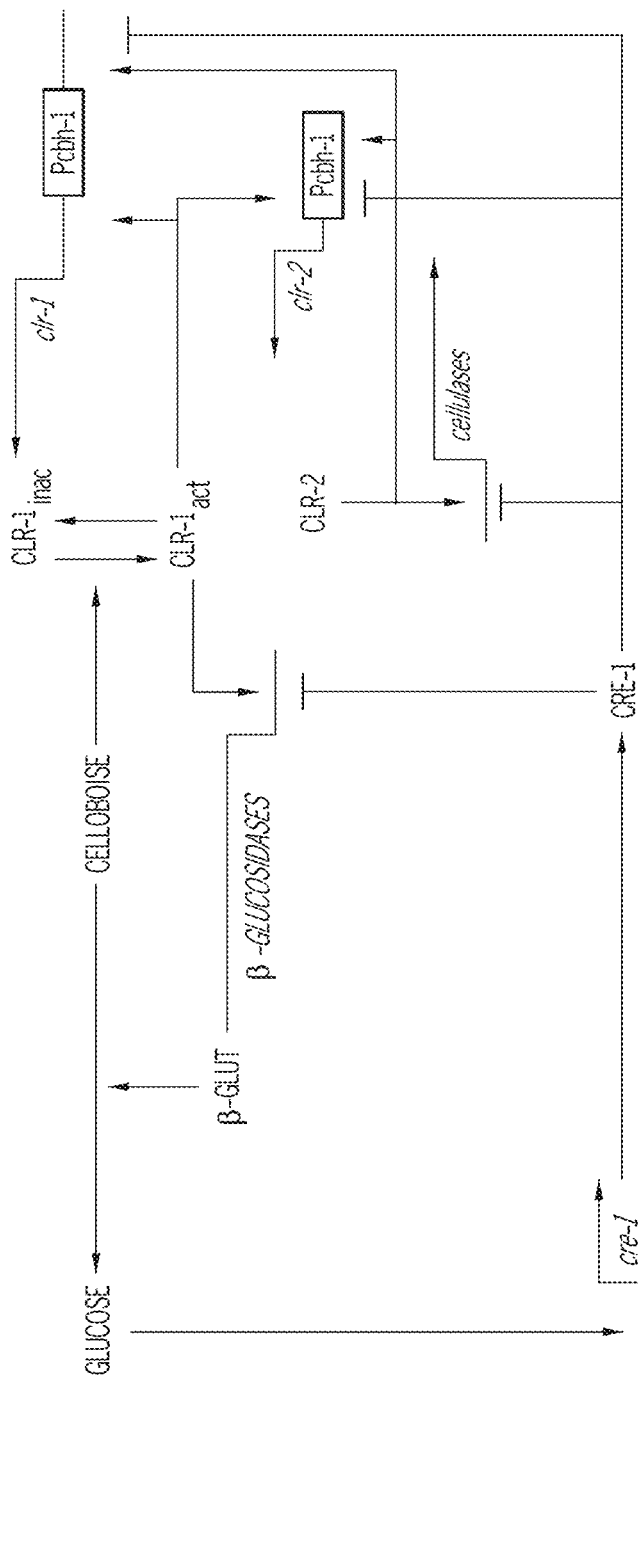
FIG. 1. Transcriptional gene network diagram of cellulase gene expression. The names written in italics are the genes, and the names written in upper cases are the proteins. Arrows indicate induction and/or synthetic positive feedback loops, and bars with blunt ends indicate inhibition. Illustrates how transcriptional activity of CLR-1 is upregulated by cellobiose.

In order to develop *N. crassa* strains with higher degrading activity of cellulose, transgenic *N. crassa* with additional clr-1, clr-2, or xlr-1 genes under the control of a promoter from one of the cellulase genes were constructed. Specifically, the promoter from cbh-1 was used to regulate the expression of the transgenes. CBH-1 is one of the cellulases, and expression is regulated by CLR-1 and CLR-2. Therefore, the novel synthetic gene network creates a positive feedback circuit to amplify the expression of the transgenes, because CLR-1 or CLR-2 can now regulate their own expressions in the network driven by the cbh-1 promoter (FIG. 1). This synthetic positive feedback loop substantially amplifies the expression of cellulases. The concept is predictably applicable to other promoters of cellulase genes that are under the control of CLR-1 and CLR-2.

Figure 2:
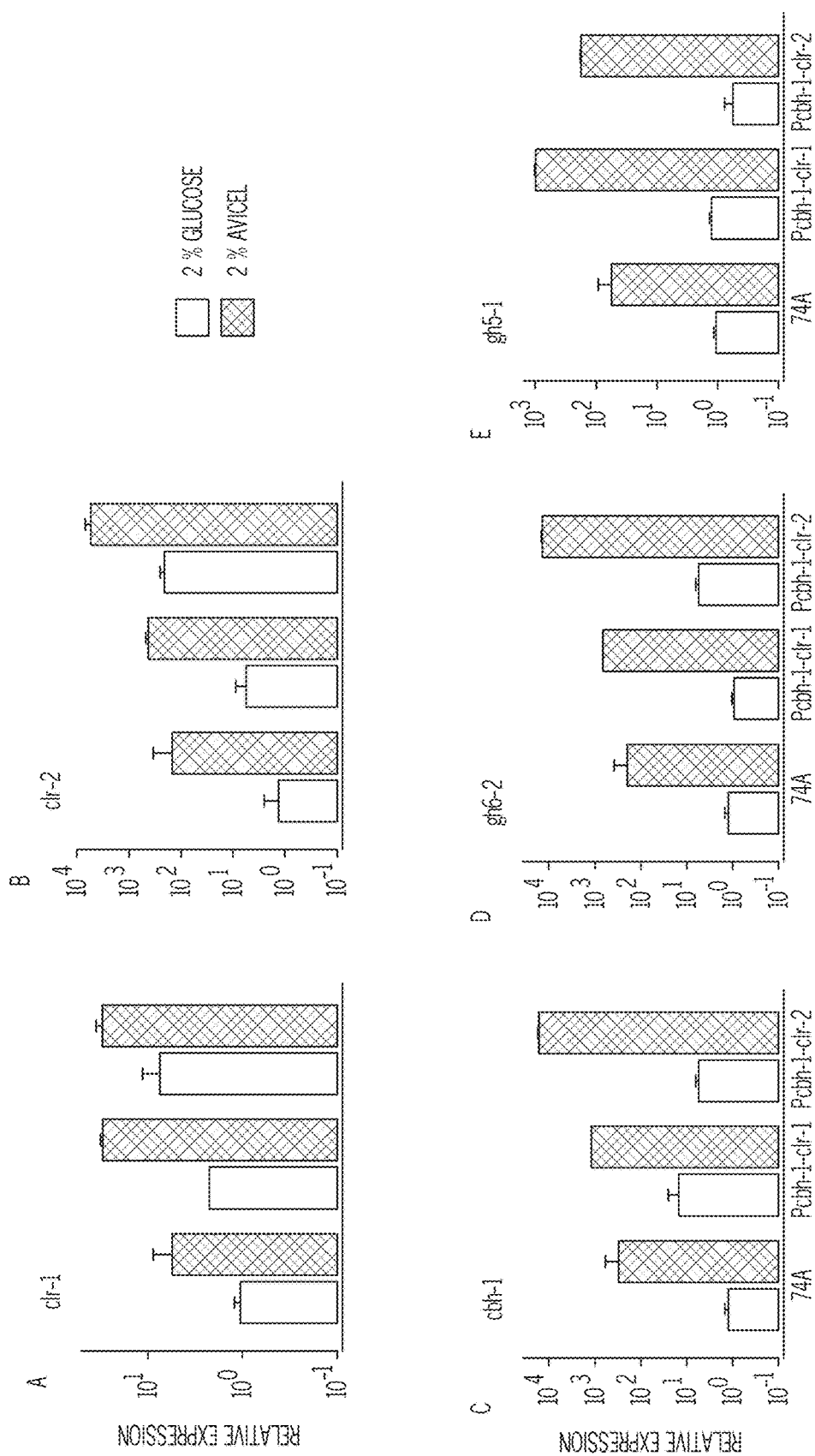
FIG. 2. (A) Bar graph showing relative mRNA expression of cellulase gene clr-1 as measured with quantitative polymerase chain reaction (qRT-PCR) in positive feedback strains cultured in either 2% glucose media or 2% avicel media; (B) bar graph showing relative mRNA expression of cellulase gene clr-2 in positive feedback strains cultured in either 2% glucose media or 2% avicel media; (C) bar graph showing relative expression of cellulase gene cbh-1; (D) bar graph showing relative expression of cellulase gene gh6-2; (E) bar graph showing relative expression of cellulase gene gh5-1. All the expressions were normalized by the expressions in wild type strain (74A); positive feedback strains are Pcbh-1-clr-1 and Pcbh-1-clr-2. The data demonstrates that expressions of cellulase genes are dramatically increased in the positive feedback strains.

According to one embodiment, the transgenic strain is engineered to comprise a synthetic positive feedback loop for a transcriptional activator of cellulase expression. A positive feedback loop is a process to return the output signal back to the input and then enhance or amplify the intensity of signal. In the novel transgenic *Neurospora* strains, the expression of the transcription factors (i.e. CLR-1 and CLR-2) is regulated under the control of cbh-1 promoter, which is a target promoter of CLR-1 and CLR-2. The output is the transcription activators themselves and which then function as the input. The expression of cellulases, however, is low in the presence of glucose in the culture media, and upregulated by addition of Avicel® microcryltalline cellulose, in the media. The expression of cbh-1 is upregulated 300-fold in the presence of avicel in wild type strain. In comparison, this induction was 20,000-fold in the clr-2 positive feedback strain (Pcbh-1-clr-2, FIG. 2). Because the positive feedback amplifies the expressions of the transcriptional activators for cellulases, not only the expression for cbh-1 but also the expression for the other cellulases are also amplified (FIG. 2).

According to one embodiment, a wild type (WT 74A,) strain is genetically modified to include at least one positive feedback loop functional to increase expression of clr-1. In one specific embodiment, transgenic strain Pcbh-1-clr-1 is engineered by fusing the clr-1 gene to the promoter of cbh-1, which is activated by CLR-2 protein. The clr-2 gene is activated by CLR-1 protein. Therefore, this particular strain creates a positive feedback loop to increase the expression of clr-1. According to another specific embodiment, Pcbh-1-clr-2 is engineered by fusing the clr-2 gene to the promoter of cbh-1, which is activated by CLR-2 protein. Therefore, this particular strain creates a positive feedback loop to increase the expression of clr-2, which subsequently activates a large number of cellulase genes. Other embodiments provide transgenic strains having reduced efficiency for metabolizing glucose and engineered with a synthetic positive feedback loop functional to increase expression of clr-2. In a specific example, the Pcbh-1-clr-2-3KO-Δcre-1 strain is engineered such that the clr-2 positive feedback loop is implemented in a quadruple knockout strain (ie. triple beta-glucosidase KO; cre-1KO). The triple beta gluosidase KO; cre-1KO (3KO-Δcre-1) strain is a known strain (N. Louise Glass, UC Berkeley) and has been shown to be less efficient in metabolizing glucose, which enables harvesting of both glucose and cellulases from the growth/culturing media. As a matter of convention, where strains are developed from different spores, they may be designated by a numerical suffix, such as Pcbh-1-clr-2-3KO-Δcre-1#2.

In some embodiments, the transgenic strain may be engineered to include more than one positive feedback loop for enhanced amplification of cellulase production. Positive feedback loops for transcriptional activators may be combined. For example, it is known that CLR-1, CLR-2, and XLR-1 have different target genes. Therefore, a combination of the overexpression of clr-1, clr-2, or xlr-1 may maximize the expression of cellulases. Multiple overexpression of transcriptional activators by cbh-1 promoter can be achieved by two methods. The first method is genetic crossing of the overexpression strains. The other method is to make heterokaryon strains. When hyphae of different strains of N. crassa encounter each other on their substrate there is a tendency for their cell walls and membranes to fuse forming a common cytoplasm. Fused Neurospora strains naturally exchange nuclei to form a heterokaryon with mixed genetic backgrounds.

Figure 3:
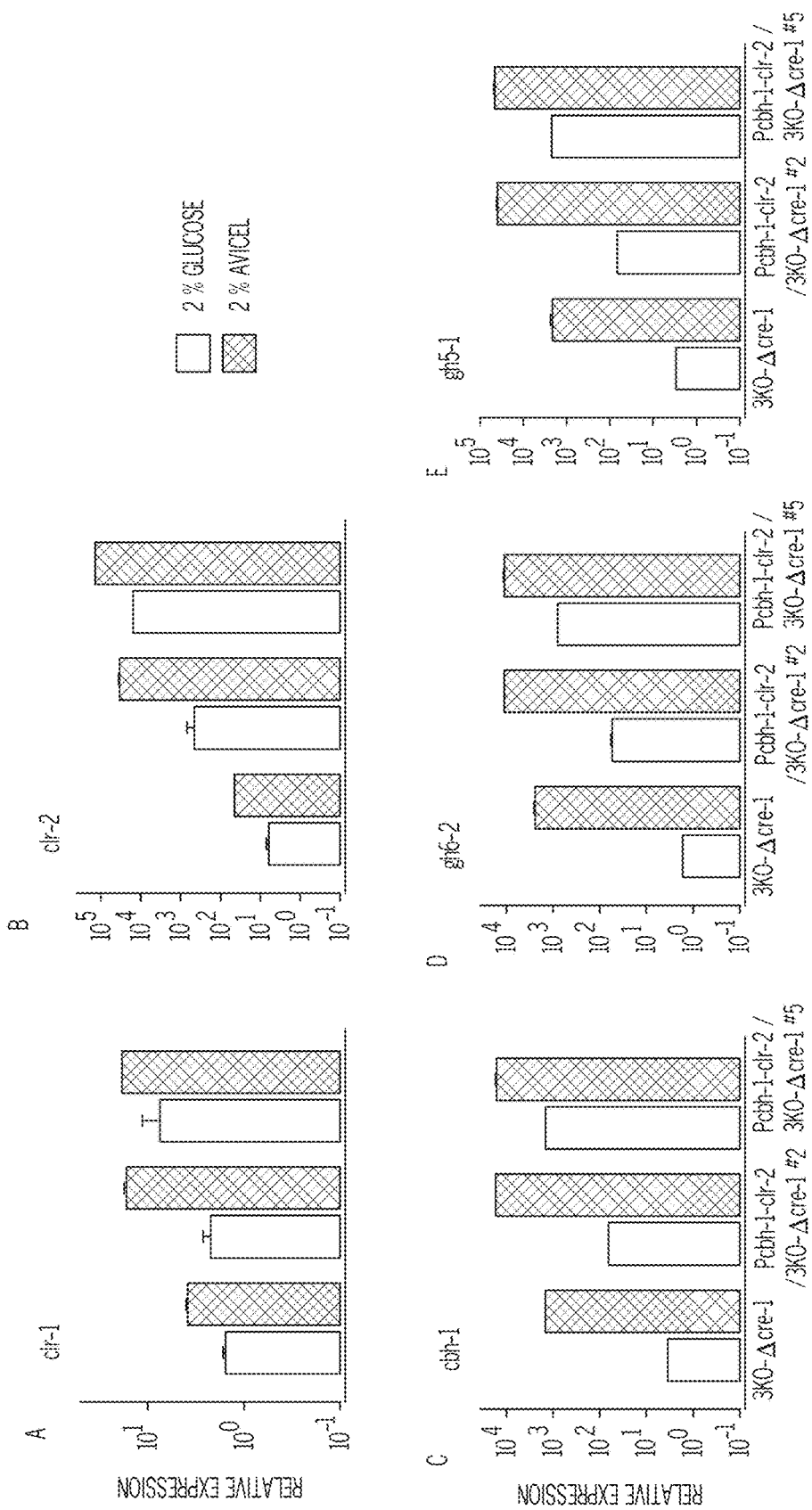
FIG. 3. (A) Bar graph showing relative mRNA expression of cellulase gene clr-1 in positive feedback strains in 3KO-Δcre-1 background cultured in either 2% glucose or 2% avicel media; (B) bar graph showing relative mRNA expression of cellulase gene clr-2 in positive feedback strains in 3KO-Δcre-1 background cultured in either 2% glucose or 2% avicel media, (C) bar graph showing relative mRNA expression of cbh-1; (D) bar graph showing relative mRNA expression of gh6-2; (E) bar graph showing relative mRNA expression of gh5-1. All the expressions were normalized by the expressions for 3KO-Δcre-1 strain; positive feedback strains are Pcbh-1-clr-2-3KO-Δcre-1#2 and Pcbh-1-clr-2-3KO-Δcre-1#5. The data demonstrates that expressions of cellulase genes are dramatically increased in the positive feedback strains.
Figure 4:
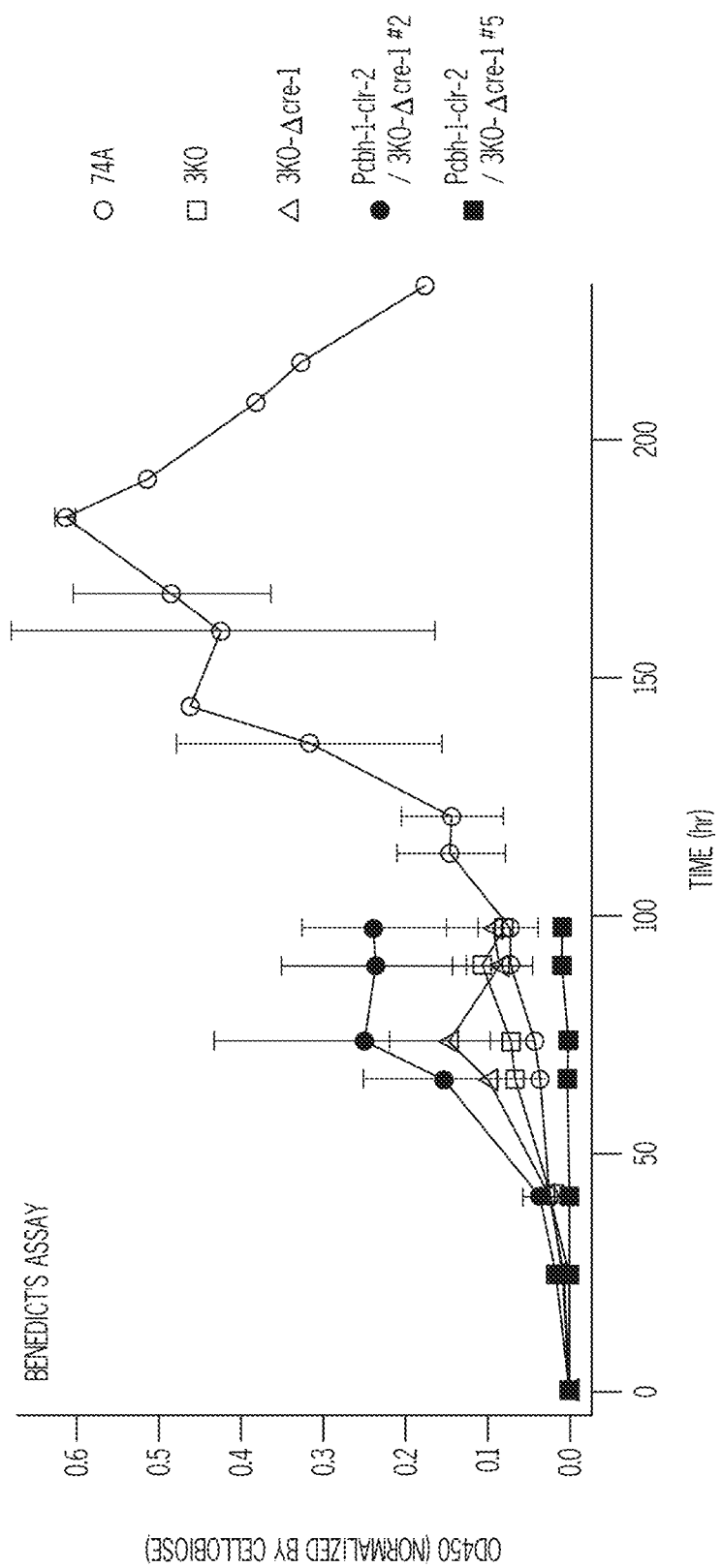
FIG. 4. Graphical representation of sugar production from cellulose measured with Benedict's reagent for five *N. crassa* strains that were cultured in 2% Avicel-containing media.

In other embodiments, positive feedback loops and gene knock out strains are combined. It is known that cellobiose, a degraded product of cellulose, functions as an inducer of lignocellulolytic gene expression in N. crassa, and deletion of three major β-glucosidases, which degrade cellobiose to glucose, increases the expression of cellulases. Furthermore, the inclusion of a deletion of the catabolite repressor gene, cre-1, in the deletion of triple β-glucosidases (3KO-Δcre-1) provides a strain that produces higher concentrations of secreted active cellulases. The combination of positive feedback loop for the transcriptional activators and 3KO-Δcre-1 resulted in a further increase of the expression of cellulases (FIG. 3). The fold changes of the cellulase genes by avicel stimulation are summarized in FIG. 5, Table 1. The degradation rate of cellobiose is slow in 3KO-Δcre-1. Therefore, cellobiose degraded from avicel accumulates in the media containing 3KO-Δcre-1 strain (FIG. 4). The accumulation of cellobiose in Pcbh-1-clr-2 with 3KO-Δcre-1 strain showed 50 times higher concentration of reducing sugars in the media compared to wild type strain (74A, FIG. 4). (Exemplary knock-out strains were obtained from Prof. N. Louise Glass of the University of California, Berkeley).

Another embodiment is directed to compositions comprising at least one transgenic strain of N. crassa engineered with at least one positive feedback loop and an amount of a culture media. Crystallized cellulose (e.g. Avicel® PH microcrystalline cellulose available from FMC Biopolymer) or glucose may be added to the media. In specific embodiments, the Avicel® is added to the compositions in a volume percentage of about 2%. In very specific embodiments, the at least one transgenic strain of N. crassa is selected from Pcbh-1-clr-1, Pcbh-1-clr-2, Pcbh-1-clr-1-3KO, Pcbh-1-clr-2-3KO, Pcbh-1-clr-1-3KO-Δcre-1, and Pcbh-1-clr-2-3KO-Δcre-1. In very specific embodiments the composition comprises Pcbh-1-clr-2-3KO-Δcre-1 and a culture media of 2% Avicel®. In other specific embodiments the composition comprises at least one strain comprising a positive feedback loop that increases expression of clh-1 and at least one strain comprising a positive feedback loop that increases expression of clh-2.

Other embodiments are directed to methods for increasing expression of at least one cellulase in a cellulase-producing fungus. Although the methods are exemplified by experiments conducted with Neurospora crassa, the process of designing a synthetic positive feedback loop for a given strain is analogous. The method comprises engineering a strain of the cellulase-producing fungus comprising a synthetic positive feedback loop functional to increase expression of a transcriptional activator of cellulase expression. According to specific embodiments, the cellulase-producing fungus comprises Neurospora crassa and the strain is engineered to comprise a synthetic positive feedback loop functional to increase expression of clr-1 and/or clr-2. In more specific embodiments the transgenic strain of N. crassa is one or more of Pcbh-1-clr-1, Pcbh-1-clr-2, Pcbh-1-clr-1-3KO, Pcbh-1-clr-2-3KO, Pcbh-1-clr-1-3KO-Δcre-1, and Pcbh-1-clr-2-3KO-Δcre-1.

Methods for producing a reducing sugar from cellulose-containing substrates are also contemplated. In specific embodiments, the methods comprise: culturing one or more transgenic strains of Neurospora crassa engineered for amplified production of cellulases in a culture media; optionally, harvesting the cellulases from the culturing media; and treating the cellulose-containing substrates with the culturing media or the harvested cellulases. A reducing sugar is any sugar that is capable of acting as a reducing agent because it has a free aldehyde group or a free ketone group. All monosaccharides are reducing sugars, along with some disaccharides, oligosaccharides, and polysaccharides. The common dietary monosaccharides galactose, glucose and fructose are all reducing sugars. The disaccharides cellobiose and maltose are also reducing sugars. According to some embodiments, the engineered transgenic strains of N. crassa comprise one or more synthetic positive feedback loops functional for increasing expression of clr-1 and/or clr-2. In very specific embodiments, the engineered strains comprise one or more of Pcbh-1-clr-1, Pcbh-1-clr-2, Pcbh- 1-clr-1-3KO, Pcbh-1-clr-2-3KO, Pcbh-1-clr-1-3KO-Δcre-1, and Pcbh-1-clr-2-3KO-Δcre-1.

Many reducing sugars are also fermentable sugars. A fermentable sugar is any sugar that can be metabolized by yeast to form alcohol, typically ethanol. Most strains of yeast prefer glucose. According to one specific embodiment, the engineered strain of *N. crassa* comprises Pcbh-1-clr-2-3KO-Δcre-1. The 3KO-Δcre-1 strain is known to increase the concentration of glucose in the culture media. By utilizing the combined strain, both excess glucose and cellulases may be harvested from the culture media. According to one specific embodiment, the Pcbh-1-clr-2-3KO-Δcre-1 strain accumulates cellobiose in the culturing media. Cellobiose is commonly used as a sweetening agent or as a fermentable intermediate in brewing. Cellobiose may be fermented with the thermotolerant methylotrophic yeast *Hansenula polymorpha* or genetically engineered *Saccharomyces cerevisiae* which express cellodextrin transporters from *N. crassa*.

Methods are provided for producing cellulosic ethanol from cellulose-containing substrates. One embodiment of the methods comprise: culturing one or more transgenic strains of *Neurospora crassa* engineered for amplified production of cellulases in a culture media; optionally, harvesting the cellulases from the culturing media; treating the cellulose-containing substrates with the culturing media or the harvested cellulases to produce a fermentable sugar; fermenting the sugar by treatment with a yeast; and distilling the cellulosic ethanol. In specific embodiments, the engineered transgenic strain of *N. crassa* comprises one or more synthetic positive feedback loops functional for increasing expression of clr-1 or clr-2. According to very specific embodiments, the engineered strain of *N. crassa* comprises one or more of Pcbh-1-clr-1, Pcbh-1-clr-2, Pcbh-1-clr-1-3KO, Pcbh-1-clr-2-3KO, Pcbh-1-clr-1-3KO-Δcre-1, and Pcbh-1-clr-2-3KO-Δcre-1.

According to one embodiment, biofuel produced from batch degradation of cellulose to produce fermentable sugars is provided. Cellulosic ethanol is a type of biofuel produced from degradation of lignocellulose, a structural material that comprises much of the mass of plants. Lignocellulose is composed mainly of cellulose, hemicellulose and lignin. Corn stover, *Panicum virgatum* (switchgrass), *Miscanthus* grass species, wood chips and the byproducts of lawn and tree maintenance are some of the more popular cellulosic materials that may be utilized for ethanol production. Production of ethanol from lignocellulose has the advantage of abundant and diverse raw material compared to sources such as corn and cane sugars. One embodiment provides methods for producing cellulosic ethanol from biomass utilizing a transgenic strain of *N. crassa* comprising at least one positive feedback loop for amplified expression of cellulases. A bio-reactor may be set up to harvest to produce and harvest the cellulases in industrial quantities, incubate the biomass in a composition of the cellulases to produce fermentable sugars, ferment the sugar to produce ethanol, and distill and collect the ethanol.

EXAMPLES

The novel transgenic strains disclosed herein were constructed by methods known in the art. Methods of construction/fabrication are not within the scope of the invention. The methods utilized by the present inventors are fully disclosed and enabled by the following publications: Colot, H. V. et al. "A high-throughput gene knockout procedure for *Neurospora* reveals functions for multiple transcription factors" *Proceedings of the National Academy of Sciences of the USA* 103 no. 27, 10352-10357 (2006); and Bardiya, N. et al. "Cyclosporin A-resistance based gene placement system for *Neurospora crassa*" *Fungal Genetics and Biology*, 44, 307-314 (2007). The entire disclosures of both references are incorporated herein in their entirety by this citation.

Example 1

This example compares the cellulase activity, as indicated by sugar production, in the culturing media of WT and transgenic strains. Generally, culturing media of each strain was harvested 7 days after growing the indicated *Neurospora* strains in the media, and cellulase activity was examined. The cultured media was incubated with 2% Avicel® (crystalized cellulose) for 6 hr. The activity of cellulase in the media was determined by degradation activity of Avicel® to reducing sugar. The reducing sugar concentration was measured at 0, 1, 2, 3, and 6 hr after incubation at 50° C. Results are shown in FIG. 6. The culture media from Pcbh-1-clr-2 and Pcbh-1-clr-2-3KO-Δcre-1 strains exhibited stronger cellulase activity compared to the media from wild type (WT) strain. Sugar production from cellulose was measured with the culture media from WT, Pcbh-1-clr-2, and Pcbh-1-clr-2-3KO-Δcre-1 strains. Compared to WT, Pcbh-1-clr-2 and Pcbh-1-clr-2-3KO-Δcre-1 strains were found to have more than 60 and 30 times sugar production, respectively (FIG. 6). This result clearly demonstrates increased secretion of cellulases from Pcbh-1-clr-2 and Pcbh-1-clr-2-3KO-Δcre-1 strains, and further confirms the usefulness of the synthetic positive feedback gene circuit to produce vast amount of cellulases. The lower cellulase activity in Pcbh-1-clr-2-3KO-Δcre-1 compared to Pcbh-1-clr-2 appears to be caused by the knockout of three β-glucosidases.

Example 2

Figures 7A, 7B:
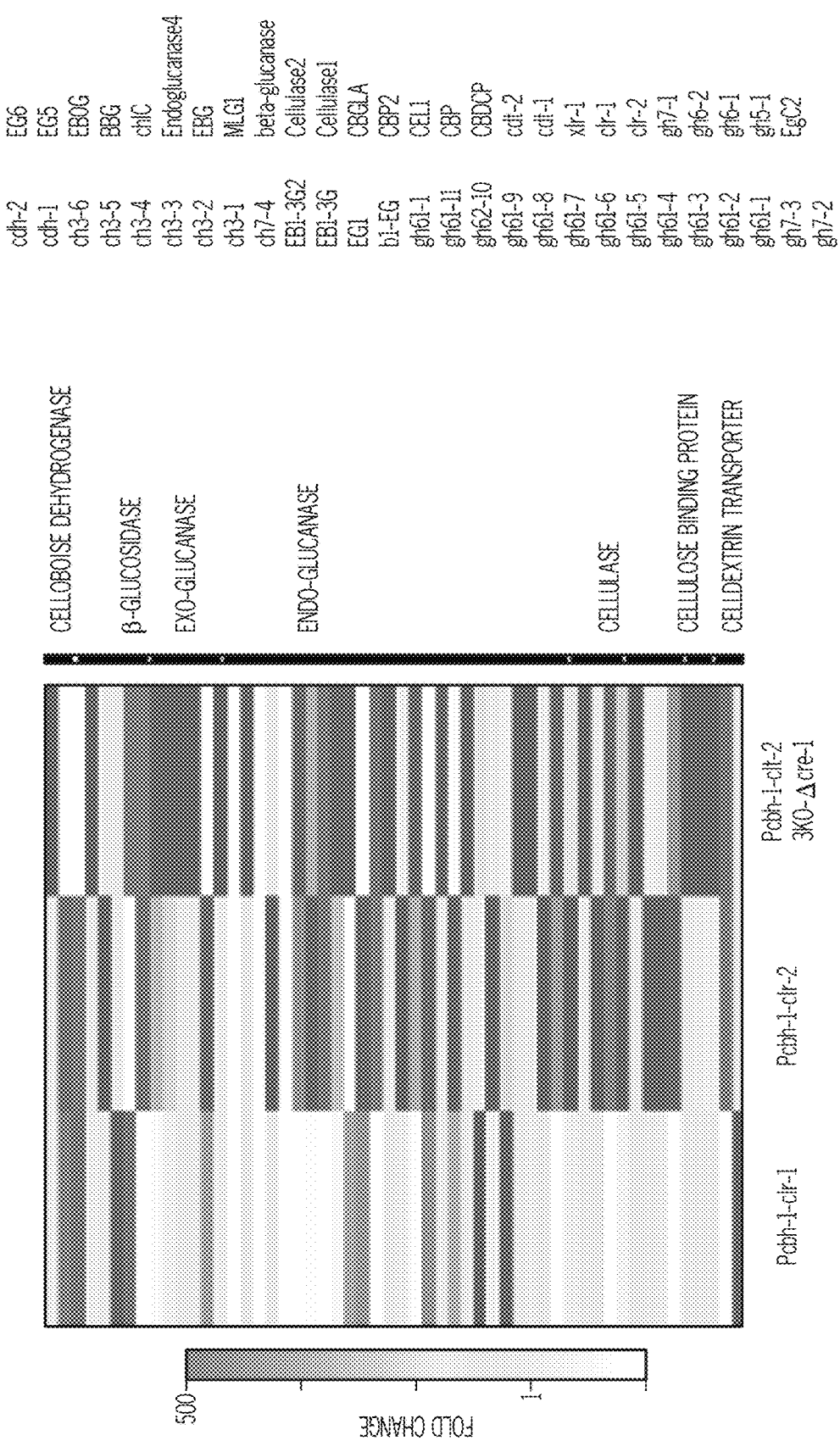
FIG. 7. Heat map of relative mRNA expression levels of cellulase-related genes in transgenic strains Pcbh-1-clr-1, Pcbh-1-clr-2, and Pcbh-1-clr-2-3KO-Δcre-1 compared to WT.
Figure 8:
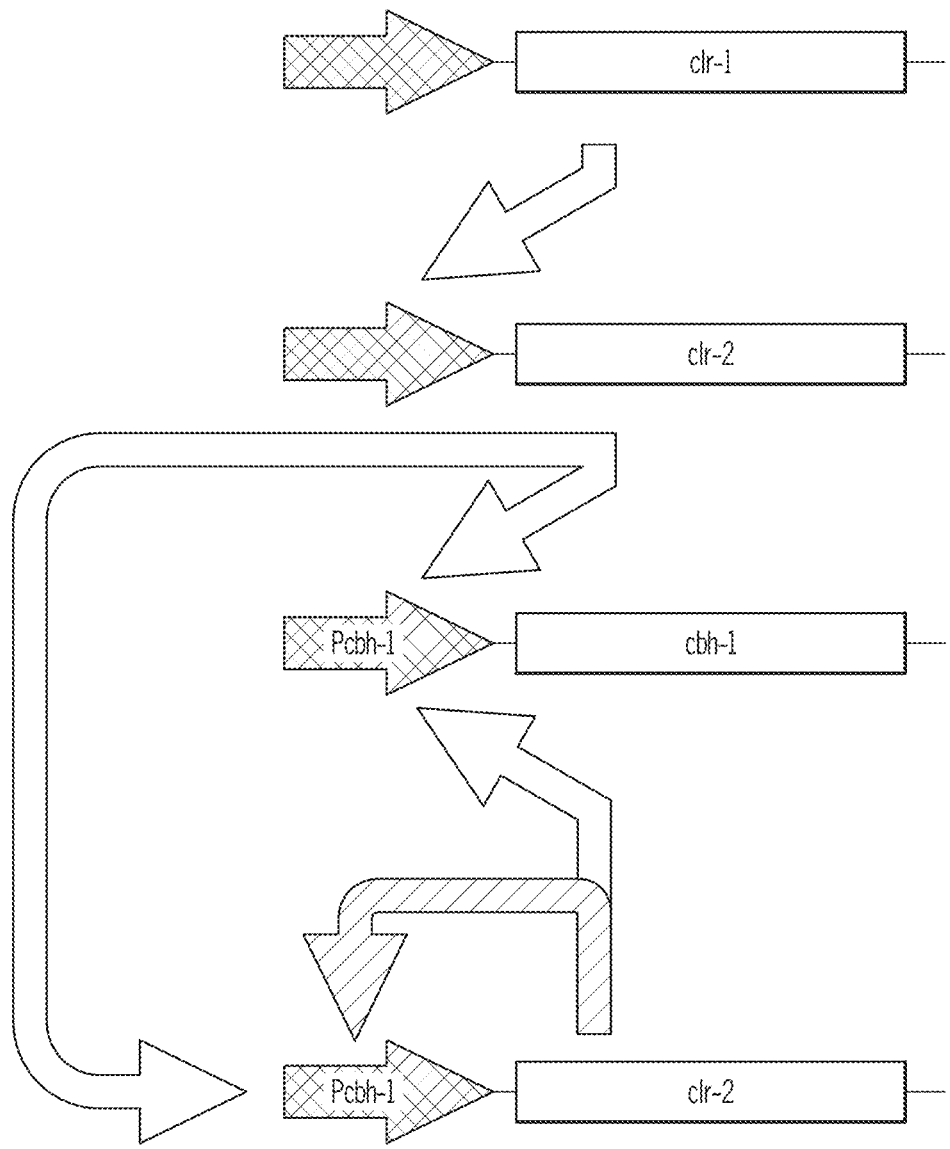
FIG. 8. A schematic illustration of the Pcbh-1-clr-2 positive feedback loop resulting in increased expression of clr-2.

This example shows relative expression levels of cellulase regulatory genes in the transgenic strains compared to WT as detected by RNA-sequencing. FIG. 7 sets forth a heat map illustrating the results. The overexpression of clr-1 or clr-2 affects broad range of cellulase-related gene expressions. 55 cellulase-related genes, including transcription factors (CLR-1 and CLR-2), cellodextrin transporters, cellulose binding proteins, and cellulases (exo-glucanase, endo-glucanase, β-glucosidase, and cellobiose dehydrogenase), were found in the genome of *N. crassa* (FIG. 7). RNA-Sequencing was performed to detect the global effect of synthetic positive gene circuits in Pcbh-1-clr-1, Pcbh-1-clr-2 and Pcbh-1-clr-2-3KO-Δcre-1 strains. A more than 2-fold higher mRNA expressions of 26, 27, and 27 out of 55 cellulase-related genes in Pcbh-1-clr-1, Pcbh-1-clr-2, and Pcbh-1-clr-2-3KO-Δcre-1 strains, respectively, was observed (FIG. 7). The degradation of cellulose involves multiple steps, and cooperation of the multiple cellulases is necessary for the efficient degradation of cellulose. Therefore, the synthetic positive feedback gene circuit with clr-1 or clr-2 provides an ideal solution to produce efficient cellulose degradation by over-expressing a large number of cellulase-related genes.

The strains are cultured with cellulose containing materials such as food wastes, wood chips, or purified cellulose. Cellulases and sugars are obtained from culturing media. Sugars in the media are then fermented with yeasts to produce bioethanol or diesel fuel component precursors.

The entire disclosures of the following academic articles are incorporated herein in their entireties by this reference: Znameroski, E. A. et al. "Induction of lignocellulose-degreading enzymes in *Neurospora crassa* by cellodextrins" *Proceedings of the National Academy of Sciences of the USA* 109, 6012-6017 (2012); Ryabova, O. B. et al. "A.A. Xylose and cellobiose fermentation to ethanol by the thermotolerant methylotrophic yeast *Hansenula polymorpha*" *FEMS Yeast Research* 4, 157-164 (2003); and Galazka et al. "Cellodextrin transport in yeast for improved biofuel production" *Science* 330, 84-86 (2010).

The invention claimed is:

1. A transgenic strain of *Neurospora crassa* engineered to comprise a synthetic positive feedback loop for a transcriptional activator of cellulase expression encoded by *N. crassa* clr-1 gene or *N. crassa* clr-2 gene, wherein the strain has been genetically modified by operably linking a promoter of a gene encoding cellobiohydrolase-1 (Pcbh-1) to the *N. crassa* clr-1 or *N. crassa* clr-2 genes.

2. A The transgenic strain of *N. crassa* according to claim 1, wherein the transgenic strain is an *N. crassa* 74A wild type (WT) strain genetically modified to comprise a synthetic positive feedback loop functional to increase expression of *N. crassa* clr-1, the transgenic strain being designated Pcbh-1-clr-1.

3. A The transgenic strain of *N. crassa* according to claim 1, wherein the transgenic strain is an *N. crassa* 74A wild type (WT) strain genetically modified to comprise a synthetic positive feedback loop functional to increase expression of *N. crassa* clr-2, the transgenic strain being designated Pcbh-1-clr-2.

4. A The transgenic strain of *N. crassa* according to claim 1, wherein the transgenic strain has reduced efficiency for metabolizing glucose and is genetically modified to comprise a synthetic positive feedback loop functional to increase expression of *N. crassa* clr-2.

5. The transgenic strain according to claim 4, wherein the transgenic strain is a triple beta glucosidase knockout and cre-1 knockout (3KO-Δcre-1) strain having reduced efficiency for metabolizing glucose, and wherein the strain is genetically modified to comprise a synthetic positive feedback loop functional to increase expression of *N. crassa* clr 2, the transgenic strain being designated Pcbh-1-clr-2-3KO-Δcre-1.

6. A composition comprising the transgenic strain of *N. crassa* according to claim 1 and culturing media.

7. The composition according to claim 6, wherein the transgenic strain of *N. crassa* is selected from:
   (a) an *N. crassa* 74A wild type (WT) strain genetically engineered to comprise Pcbh-1 operably liked to *N. crassa* clr-1, the transgenic *N. crassa* strain being designated Pcbh-1-clr-1;
   (b) an *N. crassa* 74A wild type (WT) strain genetically engineered to comprise Pcbh-1 operably linked to *N. crassa* clr-2, the transgenic *N. crassa* strain being designated Pcbh-1-clr-2;
   (c) a triple beta-glucosidase knockout *N. crassa* strain genetically engineered to comprise Pcbh-1 operably linked to *N. crassa* clr-1, the transgenic *N. crassa* strain being designated Pcbh-1-clr-1-3KO;
   (d) a triple beta-glucosidase knockout *N. crassa* strain genetically engineered to comprise Pcbh-1 operably linked to *N. crassa* clr-2, the transgenic *N. crassa* strain being designated Pcbh-1-clr-2-3KO;
   (e) a triple beta-glucosidase knockout and cre-1 knockout *N. crassa* strain genetically engineered to comprise Pcbh-1 operably linked to *N. crassa* clr-1, the transgenic *N. crassa* strain being designated Pcbh-1-clr-1-3KO-Δcre-1; and
   (f) a triple beta-glucosidase knockout and cre-1 knockout *N. crassa* strain genetically engineered to comprise Pcbh-1 operably linked to *N. crassa* clr-2, the transgenic *N. crassa* strain being designated Pcbh-1-clr-2-3KO-Δcre-1.

8. A method for increasing expression of at least one cellulase in an *N. crassa* strain, wherein said method comprises engineering an *N. crassa* strain to comprise a synthetic positive feedback loop for a transcriptional activator of cellulase expression encoded by *N. crassa* clr-1 gene or *N. crassa* clr-2 gene, wherein the strain has been genetically modified by operably linking a promoter of a gene encoding cellobiohydrolase-1 (Pcbh-1) to the *N. crassa* clr-1 or *N. crassa* clr-2 genes.

9. The method of claim 8, wherein the method comprises:
   (a) genetically engineering an *N. crassa* 74A wild type (WT) strain to comprise Pcbh-1 operably linked to *N. crassa* clr-1, the genetically engineered *N. crassa* strain being designated Pcbh-1-clr-1;
   (b) genetically engineering an *N. crassa* 74A wild type (WT) strain to comprise Pcbh-1 operably linked to *N. crassa* clr-2, the genetically engineered *N. crassa* strain being designated Pcbh-1-clr-2;
   (c) genetically engineering a triple beta-glucosidase knockout *N. crassa* strain to comprise Pcbh-1 operably linked to *N. crassa* clr-1, the genetically engineered *N. crassa* strain being designated Pcbh-1-clr-1-3KO;
   (d) genetically engineering a triple beta-glucosidase knockout *N. crassa* strain to comprise Pcbh-1 operably linked to *N. crassa* clr-2, the genetically engineered *N. crassa* strain being designated Pcbh-1-clr-2-3KO;
   (e) genetically engineering a triple beta-glucosidase knockout and cre-1 knockout *N. crassa* strain to comprise Pcbh-1 operably linked to *N. crassa* clr-1, the genetically modified *N. crassa* strain being designated Pcbh-1-clr-1-3KO-Δcre-1; and
   (f) genetically engineering a triple beta-glucosidase knockout and cre-1 knockout *N. crassa* strain to comprise Pcbh-1 operably linked to *N. crassa* clr-2, the genetically modified *N. crassa* strain being designated Pcbh-1-clr-2-3KO-Δcre-1.

10. A method for producing a reducing sugar from cellulose-containing substrates, wherein said method comprises culturing the transgenic strain of *N. crassa* of claim 1 to amplify production of cellulases in a culture medium and
    (a) harvesting the cellulases from the culture medium and treating the cellulose-containing substrates with the harvested cellulases; or
    (b) treating the cellulose-containing substrates with the cellulase-containing culture medium.

11. The method for producing a reducing sugar according to claim 10, wherein the transgenic strain of *N. crassa* is selected from:
    (a) an *N. crassa* 74A wild type (WT) strain genetically engineered to comprise Pcbh-1 operably linked to *N. crassa* clr-1, the transgenic *N. crassa* strain being designated Pcbh-1-clr-1;
    (b) an *N. crassa* 74A wild type (WT) strain genetically engineered to comprise Pcbh-1 operably linked to *N. crassa* clr-2, the transgenic *N. crassa* strain being designated Pcbh-1-clr-2;
    (c) a triple beta-glucosidase knockout *N. crassa* strain genetically engineered to comprise Pcbh-1 operably linked to *N. crassa* clr-1, the transgenic *N. crassa* strain being designated Pcbh-1-clr-1-3KO;

(d) a triple beta-glucosidase knockout *N. crassa* strain genetically engineered to comprise Pcbh-1 operably linked to *N. crassa* clr-2, the transgenic *N. crassa* strain being designated Pcbh-1-clr-2-3KO;

(e) a triple beta-glucosidase knockout and cre-1 knockout *N. crassa* strain genetically engineered to comprise Pcbh-1 operably linked to *N. crassa* clr-1, the transgenic *N. crassa* strain being designated Pcbh-1-clr-1-3KO-Δcre-1; and (f) a triple beta-glucosidase knockout and cre-1 knockout *N. crassa* strain genetically engineered to comprise Pcbh-1 operably linked to *N. crassa* clr-2, the transgenic *N. crassa* strain being designated Pcbh-1-clr-2-3KO-Δcre-1.

12. The method according to claim 11, wherein the reducing sugar comprises a fermentable sugar.

13. The method according to claim 12, wherein the fermentable sugar comprises glucose.

14. The method for producing a fermentable sugar according to claim 13, wherein the transgenic strain is Pcbh-1-clr-2-3KO-Δcre-1, and wherein the method further comprises harvesting both glucose and cellulases from the culturing medium.

15. A method for producing cellulosic ethanol from cellulose-containing substrates, wherein said method comprises:

(a) culturing the transgenic strain of *N. crassa* of claim 1 to amplify production of cellulases in a culture medium;

(b) harvesting the cellulases from the culture medium and treating the cellulose-containing substrates with the harvested cellulases to obtain a fermentable sugar, or treating the cellulose-containing substrates with the cellulase-containing culture medium to obtain a fermentable sugar;

(c) fermenting the sugar by treatment with a yeast; and (d) distilling the cellulosic ethanol.

16. The method for producing cellulosic ethanol from cellulose-containing substrates according to claim 15, wherein the transgenic strain of *N. crassa* is selected from:

(a) an *N. crassa* 74A wild type (WT) strain genetically engineered to comprise Pcbh-1 operably linked to *N. crassa* clr-1, the transgenic *N. crassa* strain being designated Pcbh-1-clr-1;

(b) an *N. crassa* 74A wild type (WT) strain genetically engineered to comprise Pcbh-1 operably linked to *N. crassa* clr-2, the transgenic *N. crassa* strain being designated Pcbh-1-clr-2;

(c) a triple beta-glucosidase knockout *N. crassa* strain genetically engineered to comprise Pcbh-1 operably linked to *N. crassa* clr-1, the transgenic *N. crassa* strain being designated Pcbh-1-clr-1-3KO;

(d) a triple beta-glucosidase knockout *N. crassa* strain genetically engineered to comprise Pcbh-1 operably linked to *N. crassa* clr-2, the transgenic *N. crassa* strain being designated Pcbh-1-clr-2-3KO;

(e) a triple beta-glucosidase knockout and cre-1 knockout *N. crassa* strain genetically engineered to comprise Pcbh-1 operably linked to *N. crassa* clr-1, the transgenic *N. crassa* strain being designated Pcbh-1-clr-1-3KO-Δcre-1; and (f) a triple beta-glucosidase knockout and cre-1 knockout *N. crassa* strain genetically engineered to comprise Pcbh-1 operably linked to *N. crassa* clr-2, the transgenic *N. crassa* strain being designated Pcbh-1-clr-2-3KO-Δcre-1.

* * * * *